United States Patent
Ward et al.

(10) Patent No.: US 7,731,715 B2
(45) Date of Patent: Jun. 8, 2010

(54) ABLATIVE TREATMENT OF ATRIAL FIBRILLATION VIA THE CORONARY SINUS

(75) Inventors: Jim Ward, Laguna Niguel, CA (US); Mathew R. Williams, New York, NY (US)

(73) Assignee: Edwards Lifesciences Corporation, Irvine, CA (US)

( * ) Notice: Subject to any disclaimer, the term of this patent is extended or adjusted under 35 U.S.C. 154(b) by 1373 days.

(21) Appl. No.: 11/009,197

(22) Filed: Dec. 10, 2004

(65) Prior Publication Data

US 2007/0208329 A1 Sep. 6, 2007

(51) Int. Cl.
*A61B 18/18* (2006.01)
(52) U.S. Cl. .............................. 606/49; 606/41; 606/50
(58) Field of Classification Search .................. 607/101, 607/102, 122; 606/41, 46, 47, 32, 45, 49–50
See application file for complete search history.

(56) References Cited

U.S. PATENT DOCUMENTS

| | | |
|---|---|---|
| 3,255,896 A | 6/1966 | Sklorz |
| 3,315,680 A | 4/1967 | Silbertrust et al. |
| 3,467,098 A | 9/1969 | Ayres |
| 3,471,215 A | 10/1969 | Snitzer |
| 3,505,046 A | 4/1970 | Phaneuf |
| 3,563,716 A | 2/1971 | Li |
| 3,624,816 A | 11/1971 | Richard et al. |
| 3,821,510 A | 6/1974 | Muncheryan |
| 3,858,577 A | 1/1975 | Bass et al. |
| 3,865,113 A | 2/1975 | Sharon et al. |
| 3,933,455 A | 1/1976 | Chown et al. |
| 4,422,719 A | 12/1983 | Orcutt |
| 4,625,724 A | 12/1986 | Suzuki et al. |
| 4,699,147 A | 10/1987 | Chilson et al. |
| 4,701,166 A | 10/1987 | Groshong et al. |
| 4,718,417 A | 1/1988 | Kittrell et al. |
| 4,777,951 A | 10/1988 | Cribier et al. |
| 4,842,390 A | 6/1989 | Sottini et al. |
| 4,860,743 A | 8/1989 | Abela |
| 4,862,886 A | 9/1989 | Clarke et al. |
| 4,878,725 A | 11/1989 | Hessel et al. |

(Continued)

FOREIGN PATENT DOCUMENTS

DE 9411754.3 12/1994

(Continued)

OTHER PUBLICATIONS

"Dissolution of Human Atherosclerotic Disease by Fiberoptic Laser-Heated Metal Cautery Cap", Lee, et al. Am. Heart J. 107,777-778, Apr. 1984.

(Continued)

*Primary Examiner*—Roy D Gibson
(74) *Attorney, Agent, or Firm*—Michael L. Crapenhoft (57) ABSTRACT

Ablation instruments and techniques are disclosed for accessing portions of the heart wall via the coronary sinus. While shielding the major portion of the sinus and/or the circumflex coronary artery from ablative energy, the present invention provides access to the heart wall to treat atrial fibrillation. In particular, the present invention provides instruments and methods for forming transmural lesions in the left atrium, such as the so-called "left isthmus block," from within the coronary sinus.

4 Claims, 8 Drawing Sheets

U.S. PATENT DOCUMENTS

| | | |
|---|---|---|
| 4,913,142 A | 4/1990 | Kittrell |
| 4,924,863 A | 5/1990 | Sterzer et al. |
| 4,929,246 A | 5/1990 | Sinofsky |
| 4,986,830 A | 1/1991 | Owens et al. |
| 5,071,417 A | 12/1991 | Sinofsky |
| 5,078,681 A | 1/1992 | Kawashima et al. |
| 5,125,925 A | 6/1992 | Lundahl |
| 5,151,096 A | 9/1992 | Khoury |
| 5,151,097 A | 9/1992 | Daikuzono |
| 5,163,935 A | 11/1992 | Black et al. |
| 5,167,686 A | 12/1992 | Wong |
| 5,207,669 A | 5/1993 | Baker et al. |
| 5,219,346 A | 6/1993 | Wagnieres et al. |
| 5,242,398 A | 9/1993 | Knoll et al. |
| 5,242,438 A | 9/1993 | Saadatmanesh et al. |
| 5,261,904 A | 11/1993 | Baker et al. |
| 5,269,777 A | 12/1993 | Doiron et al. |
| 5,306,245 A | 4/1994 | Heaven |
| 5,336,231 A | 8/1994 | Adair |
| 5,350,375 A | 9/1994 | Deckelbaum et al. |
| 5,368,564 A | 11/1994 | Savage |
| 5,380,316 A | 1/1995 | Aita et al. |
| 5,386,564 A | 1/1995 | Shearer et al. |
| 5,409,483 A | 4/1995 | Campbell et al. |
| 5,411,025 A | 5/1995 | Webster, Jr. |
| 5,423,807 A | 6/1995 | Milder |
| 5,429,483 A | 7/1995 | Tamari |
| 5,431,168 A | 7/1995 | Webster, Jr. |
| 5,431,647 A | 7/1995 | Purcell, Jr. et al. |
| 5,441,497 A | 8/1995 | Narciso, Jr. |
| 5,464,404 A | 11/1995 | Abela et al. |
| 5,471,982 A | 12/1995 | Edwards et al. |
| 5,482,037 A | 1/1996 | Borghi et al. |
| 5,500,012 A | 3/1996 | Brucker et al. |
| 5,507,725 A | 4/1996 | Savage et al. |
| 5,536,265 A | 7/1996 | Van den Bergh et al. |
| 5,542,928 A | 8/1996 | Evans et al. |
| 5,575,766 A | 11/1996 | Swartz et al. |
| 5,575,772 A | 11/1996 | Lennox |
| 5,591,129 A | 1/1997 | Shoup et al. |
| 5,628,313 A | 5/1997 | Webster, Jr. |
| 5,632,767 A | 5/1997 | Sinofsky |
| 5,643,253 A | 7/1997 | Baxter et al. |
| 5,649,923 A | 7/1997 | Gregory et al. |
| 5,653,734 A | 8/1997 | Alt et al. |
| 5,656,011 A | 8/1997 | Uihlein et al. |
| 5,681,280 A | 10/1997 | Rusk et al. |
| 5,688,264 A | 11/1997 | Ren et al. |
| 5,716,373 A | 2/1998 | Wolvek et al. |
| 5,722,401 A | 3/1998 | Pietroski et al. |
| 5,728,092 A | 3/1998 | Doiron et al. |
| 5,772,590 A | 6/1998 | Webster, Jr. |
| 5,779,646 A | 7/1998 | Koblish et al. |
| 5,779,670 A | 7/1998 | Bidwell et al. |
| 5,779,673 A | 7/1998 | Roth et al. |
| 5,782,239 A | 7/1998 | Webster, Jr. |
| 5,782,899 A | 7/1998 | Imran |
| 5,800,392 A | 9/1998 | Racchini |
| 5,800,482 A | 9/1998 | Pomeranz et al. |
| 5,800,493 A | 9/1998 | Stevens et al. |
| 5,807,395 A | 9/1998 | Mulier et al. |
| 5,823,955 A | 10/1998 | Kuck et al. |
| 5,824,005 A | 10/1998 | Motamedi et al. |
| 5,830,209 A | 11/1998 | Savage et al. |
| 5,833,682 A | 11/1998 | Amplatz |
| 5,836,941 A | 11/1998 | Yoshihara et al. |
| 5,860,966 A | 1/1999 | Tower |
| 5,860,974 A | 1/1999 | Abele |
| 5,904,147 A | 5/1999 | Conlan et al. |
| 5,908,415 A | 6/1999 | Sinofsky |
| 5,910,129 A | 6/1999 | Koblish et al. |
| 5,931,834 A | 8/1999 | Murphy-Chutorian et al. |
| 5,938,660 A | 8/1999 | Swartz et al. |
| 5,951,497 A | 9/1999 | Wallace et al. |
| 5,971,983 A * | 10/1999 | Lesh ............................ 606/41 |
| 5,980,485 A | 11/1999 | Grantz et al. |
| 5,997,527 A | 12/1999 | Gumucio et al. |
| 6,004,261 A | 12/1999 | Sinofsky et al. |
| 6,024,740 A | 2/2000 | Lesh et al. |
| 6,139,570 A | 10/2000 | Saadat et al. |
| 6,142,994 A | 11/2000 | Swanson et al. |
| 6,161,543 A | 12/2000 | Cox et al. |
| 6,237,605 B1 | 5/2001 | Vaska et al. |
| 6,270,492 B1 | 8/2001 | Sinofsky |
| 6,314,962 B1 | 11/2001 | Vaska et al. |
| 6,315,775 B1 | 11/2001 | Thielen et al. |
| 6,325,797 B1 | 12/2001 | Stewart et al. |
| 6,522,930 B1 | 2/2003 | Schaer et al. |
| 6,558,375 B1 | 5/2003 | Sinofsky et al. |
| 6,572,609 B1 | 6/2003 | Farr et al. |
| 6,579,285 B2 | 6/2003 | Sinofsky et al. |
| 6,599,288 B2 | 7/2003 | Maguire et al. |
| 6,607,520 B2 | 8/2003 | Keane |
| 6,640,120 B1 * | 10/2003 | Swanson et al. ............ 600/374 |
| 6,652,517 B1 | 11/2003 | Hall et al. |
| 6,676,656 B2 | 1/2004 | Sinofsky et al. |
| 6,752,805 B2 * | 6/2004 | Maguire et al. ................ 606/41 |
| 6,796,972 B1 | 9/2004 | Sinofsky et al. |
| 6,855,144 B2 | 2/2005 | Lesh |
| 6,942,657 B2 | 9/2005 | Sinofsky et al. |
| 2002/0022833 A1 | 2/2002 | Maguire |
| 2003/0024537 A1 * | 2/2003 | Cox et al. .................... 128/898 |
| 2003/0055422 A1 | 3/2003 | Lesh |
| 2004/0059397 A1 | 3/2004 | Sinofsky |
| 2004/0106918 A1 * | 6/2004 | Cox et al. ...................... 606/41 |
| 2004/0187875 A1 * | 9/2004 | He et al. ...................... 128/898 |

FOREIGN PATENT DOCUMENTS

| | | |
|---|---|---|
| DE | 19630255 A1 | 1/1998 |
| EP | 0311458 | 12/1989 |
| EP | 0299448 | 5/1992 |
| EP | 0792664 | 7/2002 |
| EP | 107231 | 12/2005 |
| WO | WO84/04665 | 12/1984 |
| WO | WO94/26184 | 11/1994 |
| WO | WO96/07451 | 3/1996 |
| WO | WO96/39205 | 12/1996 |
| WO | WO97/37714 | 10/1997 |
| WO | WO97/43965 | 11/1997 |
| WO | WO99/38571 | 8/1999 |
| WO | WO01/13812 | 3/2001 |

OTHER PUBLICATIONS

"Laser Recannalization of Atheromatous Vessels Using Fiberoptics", Ward, Lasers in Surgery and Medicine 4, 353-363, Dec. 1984.

"Salvage of an Ischemic Limb by Laser Angioplasty; Description of a new Technique", Ginsberg, et al. Clin. Cardiol. 7, 54-58, Jan. 1984.

"The Artery Zapper", Denise Grady, Discover, Dec. 1982.

"Application of Laser Beam in the Vessel Wall Without Interruption of Blood Flow", Armelin, et al. Circulation, 66(abstract) 11-136 (1982).

"Transluminal Laser Catheter Angioplasty", Choy, et al. Am. J. Cardiol. 50, 1199-1205, (1982).

"Laser Coronary Angioplasty: Experience with 9 Cadaver Hearts", Choy, et al. Am. J. Cardiol. 50, 1209-1211 (1982).

"Effects of Carbon Dioxide, Nd-YAG, and Argon Laser Radiation on Coronary Atheromatous Plaques", Abela, et al. Am. J. Cardiology 50, 1209-1211 (1982).

"Feasibility of Intravascular laser irradiation for in vivo visualization and therapy of cardiocirculatory diseases", Lee, et al. Am. Heart J. 103, 1076-1077(1982).

* cited by examiner

ABLATIVE TREATMENT OF ATRIAL FIBRILLATION VIA THE CORONARY SINUS

FIELD OF THE INVENTION

The technical field of the invention is cardiac surgery and, in particular, techniques and instruments for surgery on a beating heart to treat atrial fibrillation.

BACKGROUND OF THE INVENTION

Atrial fibrillation (AF) is a form of cardiac arrhythmia characterized by rapid randomized contractions of atrial myocardium, causing an irregular, often rapid ventricular rate. The regular pumping function of the atria is replaced by a disorganized, ineffective quivering. Atrial fibrillation is caused, in large part, by chaotic conduction of electrical signals through the upper chambers of the heart. Atrial fibrillation is often associated with other forms of cardiovascular disease, including congestive heart failure, rheumatic heart disease, coronary artery disease, left ventricular hypertrophy, cardiomyopathy or hypertension.

Various techniques have been proposed for the treatment of atrial fibrillation by blocking errant electrical signal conduction in the heart. For example, the "Maze procedure" was developed in the early 1990s to treat atrial fibrillation by forming a series of physical incisions (in the form of a maze) to create scar tissue in the heart that would stop or redirect the electrical impulses. Although these procedures were originally performed with a scalpel, various other techniques have also been developed to form lesions.

Researchers have come to realize that the origins of AF often lie in the left atrium in the vicinity of the pulmonary veins. A lesion encircling the pulmonary veins is currently considered to be one of the most important areas to isolate. Additionally, a second lesion extending from the pulmonary veins to the mitral valve annulus is also considered advantageous. This mitral valve annulus lesion is sometimes referred to as the "left isthmus block."

Typically, such lesions are formed from within the heart (by applying a scalpel or other ablation instrument to the endocardial tissue). In fact, it is becoming increasingly commonplace for patients undergoing open heart cardiac surgery (e.g., for mitral valve replacement) to also have an ablative procedure if they have a history of AF.

These procedures are very invasive (requiring a sternotomy, cardiopulmonary bypass, cardioplegic arrest, and cardiac incisions) to enter the left atrium of the heart and create the lesions. Despite various advances in rapid lesion-forming devices (such as ultrasound, radio-frequency (RF), laser and cryogenic instruments), open heart surgery has a significant morbidity and remains a procedure of last resort for treating AF except when other conditions mandate such surgery.

Considerable effort has been made to find ways to treat atrial fibrillation without cardiac arrest and open-heart surgery. For example, light based systems for creating lesions on the outer surface of the heart have been disclosed in U.S. Pat. No. 6,558,375 entitled "Surgical Ablation Instruments for Forming an Encircling Lesion" herein incorporated by reference in its entirety. In such systems, radiant energy is applied to the epicardium to induce a transmural lesion. These systems permit the surgeon to encircle the pulmonary veins with an instrument and create a lesion by photoablation. Others have proposed similar epicardial devices based on ultrasound and the like. Such systems avoid the need to stop the heart (cardioplegic arrest).

Although epicardial ablation devices have been proposed to create lesions around the pulmonary veins, access to the regions of the atrium extending from the pulmonary veins to the mitral valve annulus remains a problem, primarily because other cardiac structures can preclude epicardial access. In particular, the coronary sinus and circumflex artery lie directly above the target region for creation of the left isthmus block or lesion. If ablative energy is applied to the circumflex coronary artery in an effort to form an atrial lesion, stenosis of this blood vessel can occur and potentially result in a myocardial infarction or even death.

Thus, there exists a need for better ablation instruments and techniques. In particular, instruments capable of forming lesions extending from the pulmonary veins to the mitral valve annulus would satisfy an important need in the field.

SUMMARY OF THE INVENTION

Ablation instruments and techniques are disclosed for accessing portions of the heart wall via the coronary sinus. While shielding the major portion of the sinus and/or the circumflex coronary artery from ablative energy, the present invention provides access to the left heart wall to treat atrial fibrillation. In particular, the present invention provides instruments capable of forming transmural lesions in the left atrium, such as the so-called "left isthmus block," from the coronary sinus.

In one aspect of the invention, methods for forming cardiac lesions are disclosed in which ablative energy is applied to the heart from within the coronary sinus. Such methods can be practiced in conjunction with epicardial ablation of a lesion around the pulmonary veins. In one approach, the pulmonary vein lesion is formed and then an ablation instrument is introduced into the right atrial appendage. The instrument is then passed through the right atrium and into the coronary sinus. A purse string suture can be used to maintain hemostatis. Once properly situated, the ablation instrument is activated to form a lesion from the pulmonary vein encircling lesion to the mitral valve annulus.

In another aspect of the invention, devices are disclosed for placement within the coronary sinus to form a lesion in the left atrium that can extend from the pulmonary veins to the mitral valve annulus. The device can include an anchoring structure, such as a balloon, and an ablation element for heating (or freezing) a portion of the atrial wall. The device can further include a shield element to further protect the coronary sinus from ablation. Asymmetric balloon structures can also be used for shielding.

In one embodiment, an ablation system can include a diode laser, one or more optical fibers and a light-directing tip structure. The light directing optics can provide sidewise projection of ablative energy as a small spot. By rotating the ablation instrument about its elongate axis, such a spot-shaped beam can form a linear lesion in the heart wall. Alternatively, the light-directing tip can include an optical element that spreads the ablative radiation into a fan-shaped beam to produce a linear or arc-shaped transmural lesion without the need for instrument rotation.

In addition, other ablation systems can be used in lieu of optical radiation. The ablation system can also be ultrasound, radio-frequency (RF), laser or cryogenic system. The instruments of the present invention can also include physical markers, such as protuberances or ridges, that facilitate placement or orientation of the instrument in the coronary sinus by "touch" when the present invention is used during open chest procedures. By palpitating the coronary sinus from the outside, the surgeon can use the markers to locate the instrument within the sinus and ensure its proper positioning, e.g., to direct ablative energy towards the atrium target region and not the coronary sinus itself or the coronary arteries.

The present invention is useful in performing surgery on a "beating" heart and can be practiced as part of a sternotomy procedure or in less invasive procedures. Ideally, the invention will permit thoracoscopic treatments for atrial fibrillation via small incision surgery without opening the patient's chest.

DETAILED DESCRIPTION OF THE INVENTION

The present invention generally provides ablation instruments and techniques for accessing portions of the heart wall via the coronary sinus. While shielding the major portion of the sinus and/or the circumflex coronary artery from ablative energy, the present invention provides access to the heart wall to treat atrial fibrillation. In particular, the present invention provides instruments and methods for forming transmural lesions in the left atrium, such as the so-called "left isthmus block," from within the coronary sinus.

Figure 1A:
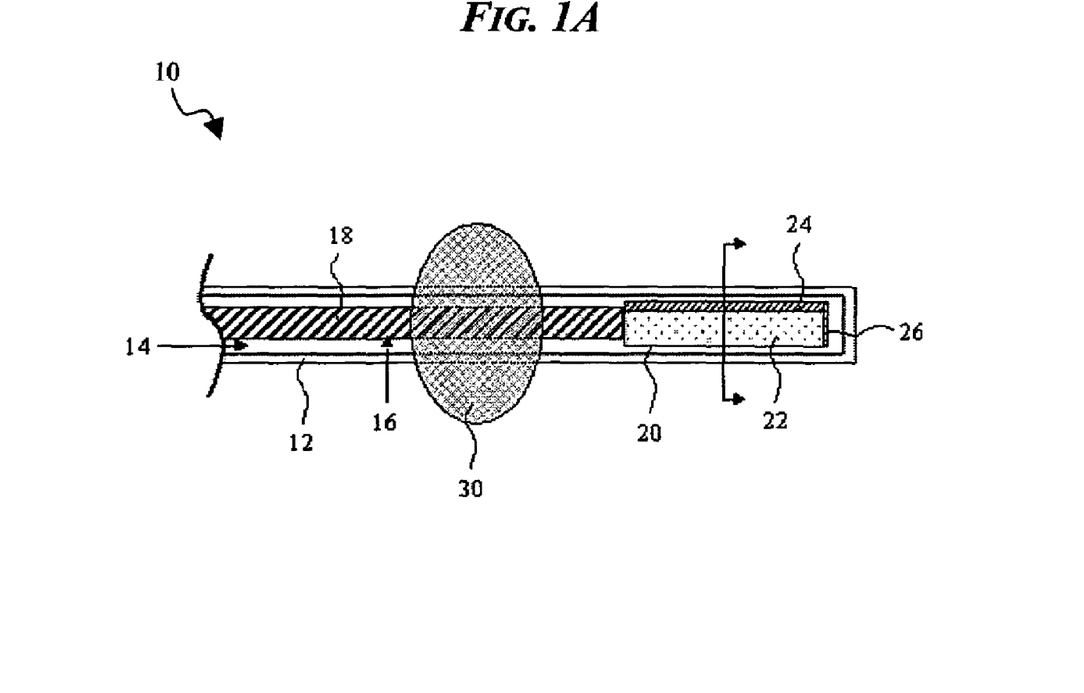
FIG. 1A is a cross-sectional side view of one embodiment of a tip portion of an ablation instrument in accordance with the present invention.
Figure 1B:
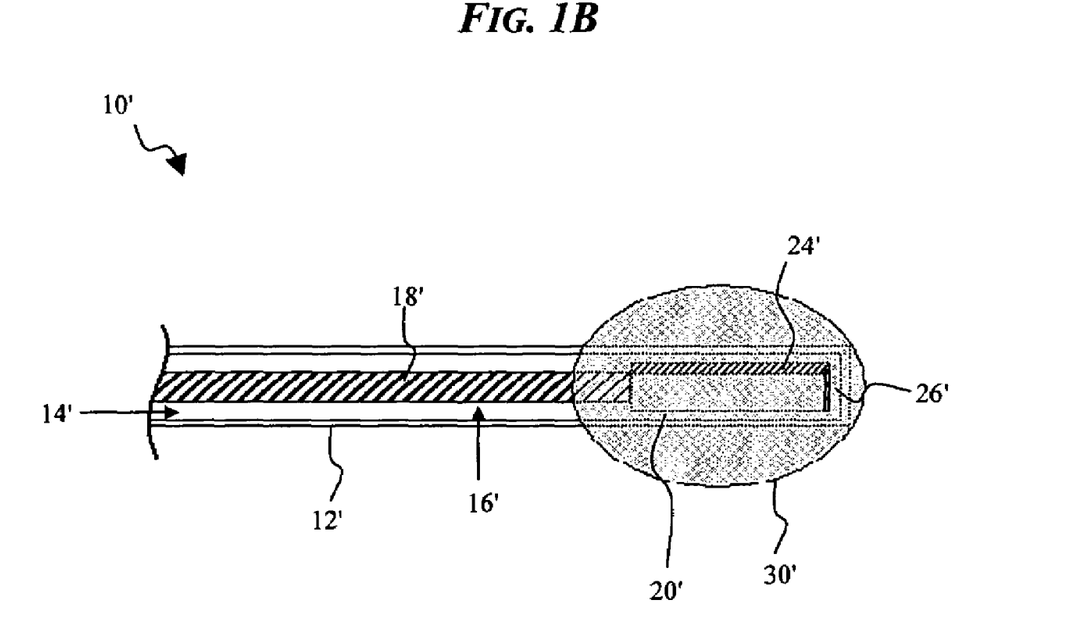
FIG. 1B is a cross-sectional side view of another embodiment of a tip portion of an ablation instrument in accordance with the present invention.

While various ablation instruments can be used with the present invention, FIGS. 1A-1B illustrate one exemplary embodiment of an ablation instrument 10. As shown, the instrument 10 generally includes an outer housing 12 with an inner lumen 14 extending therethrough, and an ablative element 16 formed or disposed within the inner lumen 14 in the housing 12 for delivering radiant energy to a target ablation site.

The outer housing 12 can have a variety of configurations, but it preferably has a generally elongate shape and it is formed from a flexible material. The outer housing 12 can also optionally be malleable to allow the shape of the outer housing 12 to conform to various anatomical shapes as needed. In an exemplary embodiment, the outer housing 12 is formed from a polymeric, electrically nonconductive material, like polyethylene (PET), polytetrafluoroethylene (PTFE), FEP, PFA, urethane, polyurethane, or PVC, which can withstand tissue coagulation temperatures without melting and provides a high degree of laser light transmission. Preferably, the housing 12 is made of Teflon® (one commercial form of PTFE) tubes and/or coatings. The use of Teflon® improves the procedures by avoiding the problem of fusion or contact-adhesion between the ablative element 16 and the cardiac tissue during usage. While the use of Teflon® avoids the problem of fusion or contact-adhesion, the ablation instrument 10 does not require direct contact with the tissue to effect a therapeutic or prophylactic treatment.

The outer housing 12 can also optionally include an anchoring element to maintain the outer housing 12 in a fixed position adjacent the ablative site. By way of non-limiting example, as shown in FIG. 1A, the outer housing 12 includes an expandable element 30 for anchoring the distal portion of the ablative element 16 adjacent to a target ablation site. While the expandable element 30 can be formed anywhere on the ablation instrument 10, FIG. 1A illustrates the element 30 as a balloon disposed at a location proximal to the distal end of the instrument 10 and proximal to the light-directing tip 20 of the ablative element 16, which will be described in more detail below. FIG. 1B illustrates another embodiment in which the element 30' is a balloon that is disposed around the distal end of the instrument 10' such that it is positioned around the light-directing tip 20' of the ablative element 16'. Referring back to FIG. 1A, the balloon 30 can be inflated by various mechanisms known in the art. For example, it can be inflated via a second lumen extending (not shown) through the outer housing 12 for delivering an inflation fluid to the balloon 30. Various other mechanical expansion elements can be used in lieu of the illustrated balloon to provide the same anchoring function.

In addition to anchoring the outer housing 12 at a fixed location, the anchoring element 30 can also function to control delivering ablative energy from the ablative element 16 to the target ablation site. In particular, the balloon 30 can have various shapes, including a symmetrical or asymmetrical shape, and the size and/or shape of the balloon can be adjusted to position the ablative element 16 at a particular location relative to the target ablation site. This control permits the radiant energy to be dynamically changed to specifically target the desired ablation site while protecting non-targeted tissue from the ablative energy.

In another embodiment, the ablative element can be a radiant energy source disposed within the balloon 30 and/or the housing 12, which can include a coating or shield for protecting non-targeted tissue from ablative energy and/or for directing ablative energy to the target ablation site. For example, the housing 12 or balloon 30 can be formed from an opaque or semi-opaque material, such as PTFE, and it can include an optically transparent window that allows radiant energy to pass therethrough. Alternatively, the housing 12 or balloon 30 can be formed from an optically transparent material, and an opaque or semi-opaque coating can be formed or disposed thereon such that energy can only pass through the non-coated portion. The shield can also or alternatively be a reflective material that is effective to direct the radiant energy toward the target ablation site. Regardless, the shield is preferably located on the housing 12 and/or balloon 30 such that radiant energy will be directed only toward the target ablation site while other non-targeted tissue is protected.

A person skilled in the art will appreciate that a variety of other techniques can be used to anchor the ablation instrument 10 adjacent to a target ablation site, to shield non-targeted tissue from ablative energy, and/or to control delivery of ablative energy to the target ablation site. Moreover, a variety of other expandable elements, such as an expandable cage, can be used in place of an expandable balloon 30.

In use, the outer housing 12 can function as a guide device for the ablative element 16. That is, once the outer housing 12 is stationed relative to the targeted tissue site, the ablative element 16 can be advanced through the housing 12 to position the ablative element 16 in a proper orientation to facilitate ablation of the targeted tissue. While not shown, the outer housing 12 can include a lever or other device for controlling movement of the ablative element 16 within the outer housing 12. The outer housing 12 can also include a variety of other features to facilitate use of the device. Alternatively, the ablative element can be fixed within the housing 12.

The ablative element 16 can also have a variety of configurations. In the embodiments shown in FIGS. 1A, 1C, and 1D the ablative element 16 includes a light transmitting optical fiber 18 and a light-directing tip 20. The light transmitting optical fiber 18 is adapted to receive ablative energy from a penetrating light source and it is effective to deliver the energy to the light-directing tip 20, wherein the light is diffused throughout the tip 20 and delivered to a target ablation site. In an exemplary embodiment, the light transmitting optical fiber 18 includes an optically transmissive core surrounded by a cladding and a buffer coating (not shown). The optical fiber 18 should be flexible to allow the fiber 18 to be slidably moved with respect to the outer housing 12. In use, the light transmitting optical fiber 18 conducts light energy in the form of ultraviolet light, visible light, near infrared, infrared radiation, or coherent light, e.g., laser light. The fiber 18 can be formed from glass, quartz, polymeric materials, or other similar materials which conduct light energy.

Figure 1C:
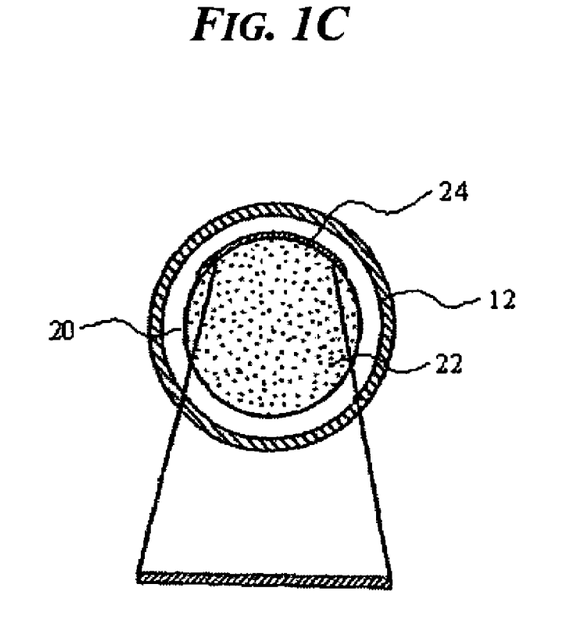
FIG. 1C is a schematic, cross-sectional view taken across line B-B of the tip portion of the ablation instrument shown in FIG. 1A, showing radiant energy being emitted to form a lesion.
Figure 1D:
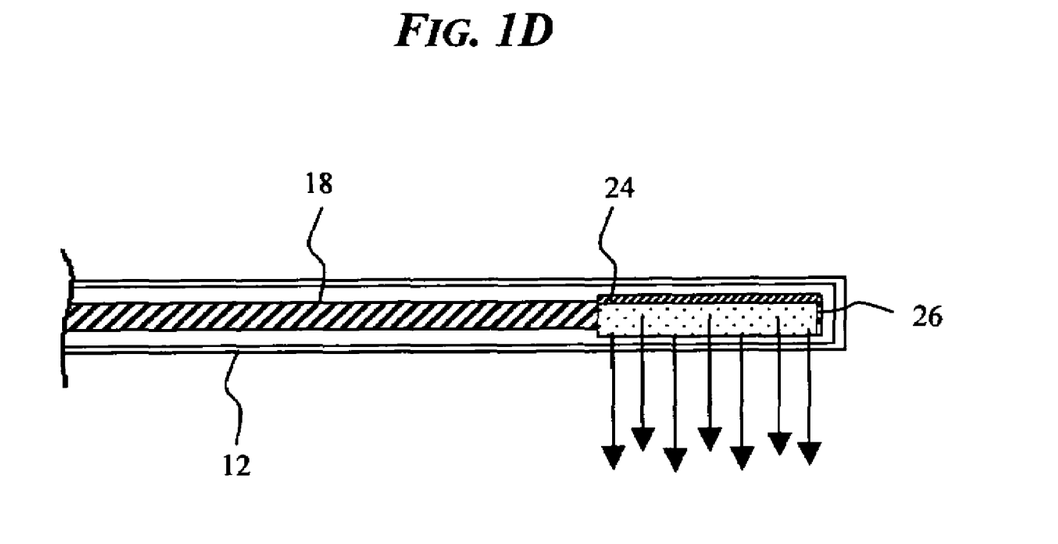
FIG. 1D is a schematic, side view of a tip portion of an ablation instrument shown in FIG. 1A, showing radiant energy being emitted to form a linear lesion.

The light-directing tip 20, which extends distally from the optical fiber 18, can also have a variety of configurations but it is preferably formed from a transmissive tube having a light scattering medium 22 disposed therein. The scattering medium 22 disposed within the light-directing tip 20 can be formed from a variety of materials, and it preferably includes light scattering particles. The refractive index of the scattering medium 22 is, however, preferably greater than the refractive index of the outer housing 12. Preferred scattering medium 22 includes polymeric material, such as silicone, epoxy, or other suitable liquids. The light scattering particles can be formed from, for example, alumina, silica, or titania compounds, or mixtures thereof. Preferably, the light-directing tip 20 is completely filled with the scattering medium 22 to avoid entrapment of air bubbles.

In use, light propagating through the optical fiber 18 is transmitted through the light-directing tip 20 into the scattering medium 22. The light is scattered in a cylindrical pattern along the length of the light-directing tip 20 and, each time the light encounters a scattering particle, it is deflected. At some point, the net deflection exceeds the critical angle for internal reflection at the interface between the housing 12 and the scattering medium 22, and the light exits the housing 12 to ablate the tissue.

Figure 1E:
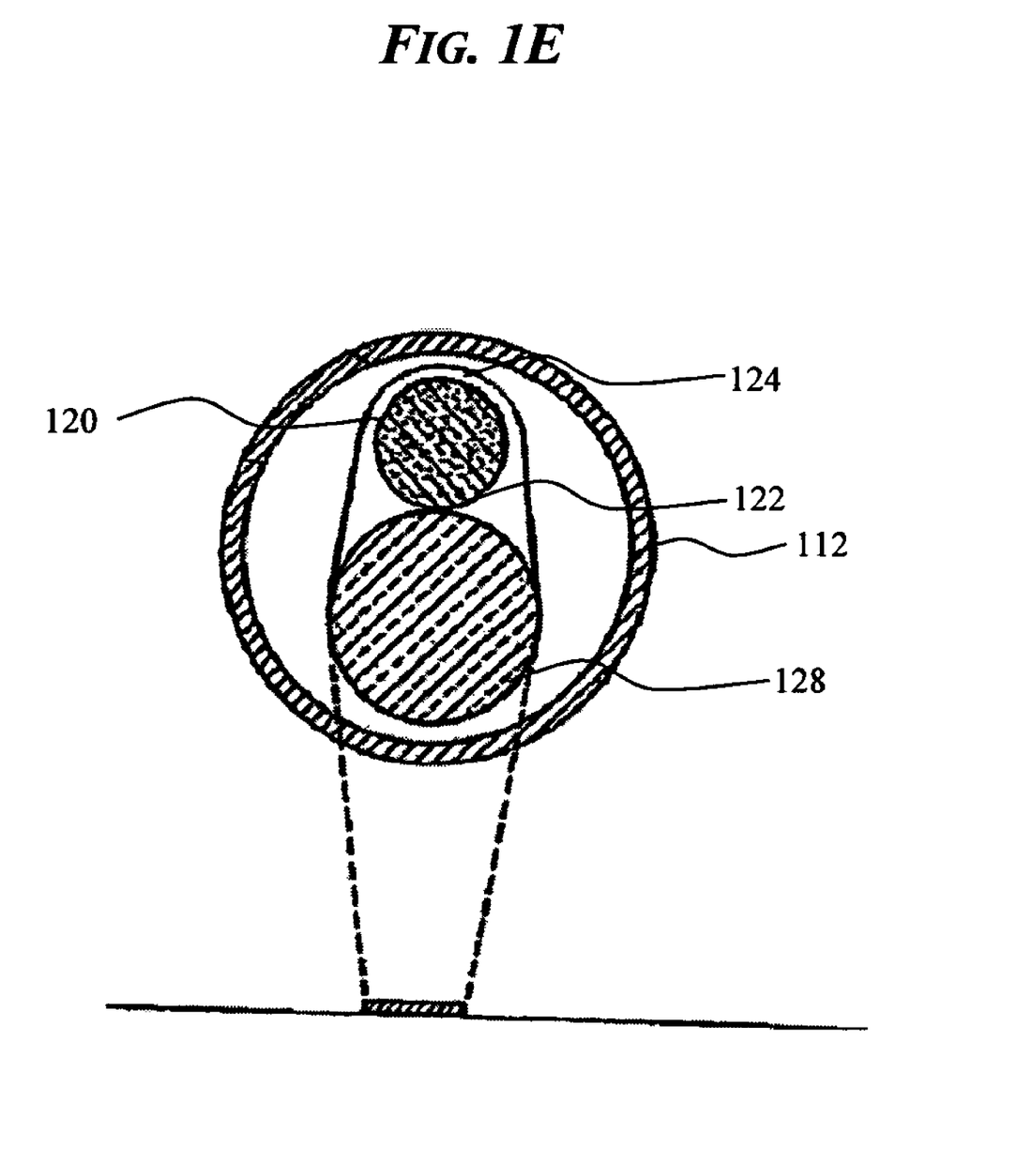
FIG. 1E is a schematic, cross-sectional view of a tip portion of an ablation instrument emitting radiant energy to form a lesion in accordance with another embodiment of the present invention.
Figure 1F:
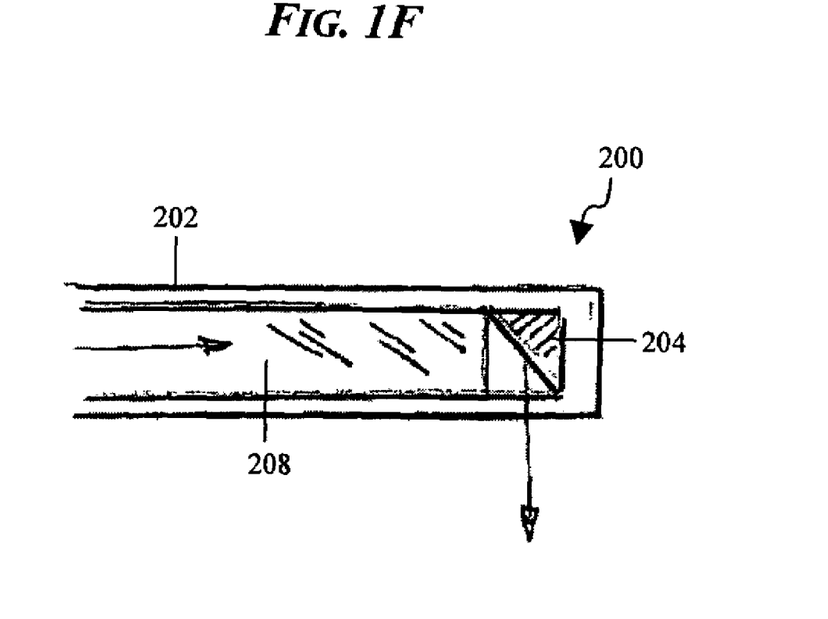
FIG. 1F is a schematic, cross-sectional view of a tip portion of an ablation instrument with a reflector disposed therein in accordance with yet another embodiment of the present invention.

As is further shown in FIGS. 1A, 1C and 1D, the light-directing tip 20 can also optionally include a reflective end 26 and/or a reflective coating 24 extending along a length of one side of the light-directing tip 20 such that the coating 24 is substantially diametrically opposed to the target ablation site. The reflective end 26 and the reflective coating 24 interact to provide a substantially uniform distribution of light throughout the light-directing tip 20. The reflective end 26 and the reflective coating 24 can be formed from, for example, a mirror or gold coated surface. While FIGS. 1A, 1C, and 1D illustrate the coating 24 extending along one side of the length of the diffusing tip 20, a person having ordinary skill in the art will appreciate that the light-directing tip 20 can be coated at different locations relative to the target ablation site. For example, the reflective coating 24 can be applied over 50% of the entire diameter of the light-directing tip 20 to concentrate the reflected light toward a particular target tissue site, thereby forming a lesion having a relatively narrow width. In another embodiment, as illustrated in FIG. 1E, the ablative element 116 can further include a longitudinally extended lens element 128, such that light scattered by the scattering medium 122 is not only reflected by reflector 124, but it is also confined to a narrow angle to form a fan-shaped beam that produces a linear lesion. While not shown, the lens 128 can alternatively be configured to form a fan-shaped beam that produces an arc-shaped lesion extending in a direction that is substantially transverse to a longitudinal axis of the tip 120, or the lens 128 and/or coating 124 can be adapted to form a small spot-shaped lesion, such that rotation of the ablative element 116 is effective to form an arc-shaped linear lesion.

Figure 1G:
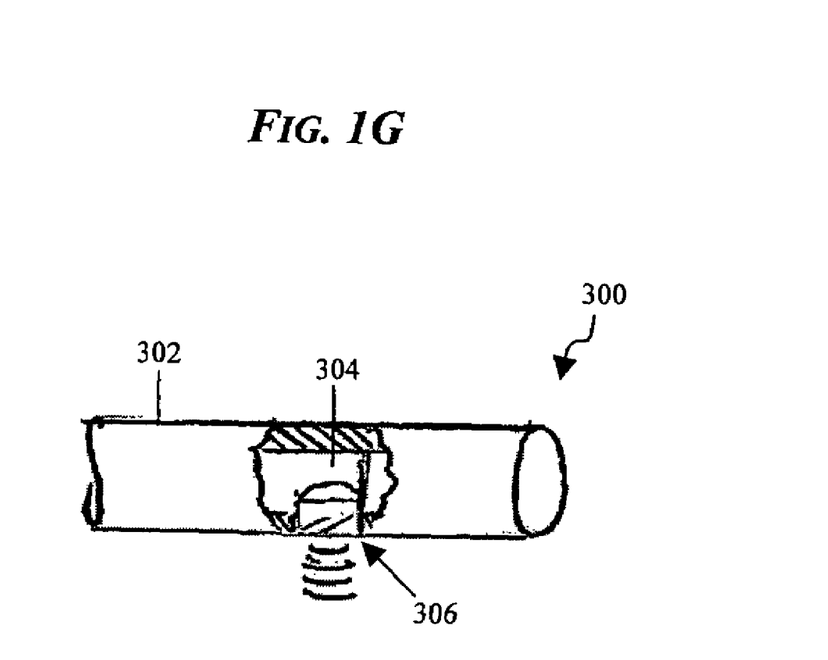
FIG. 1G is a schematic, partially cross-sectional view of a tip portion of yet another embodiment of an ablation instrument for delivering ultrasound energy to a target ablative site in accordance with the present invention.
Figure 1H:
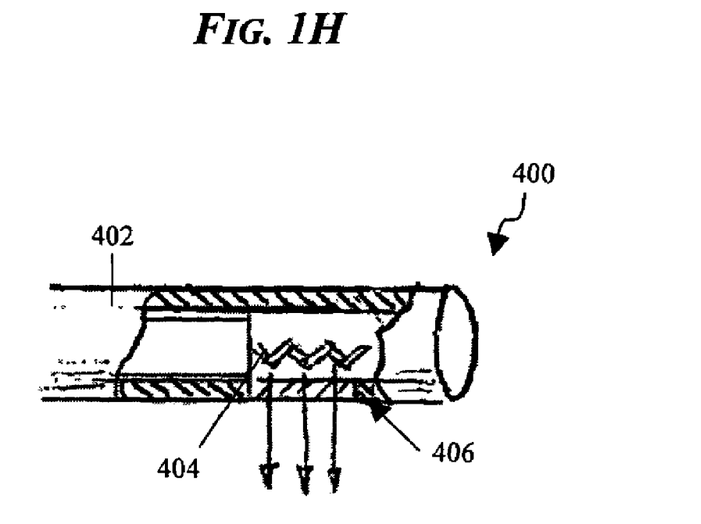
FIG. 1H is a schematic, partially cross-sectional view of a tip portion of an ablation instrument for delivering RF or microwave energy to a target ablation site in accordance with another embodiment of the present invention.
Figure 1I:
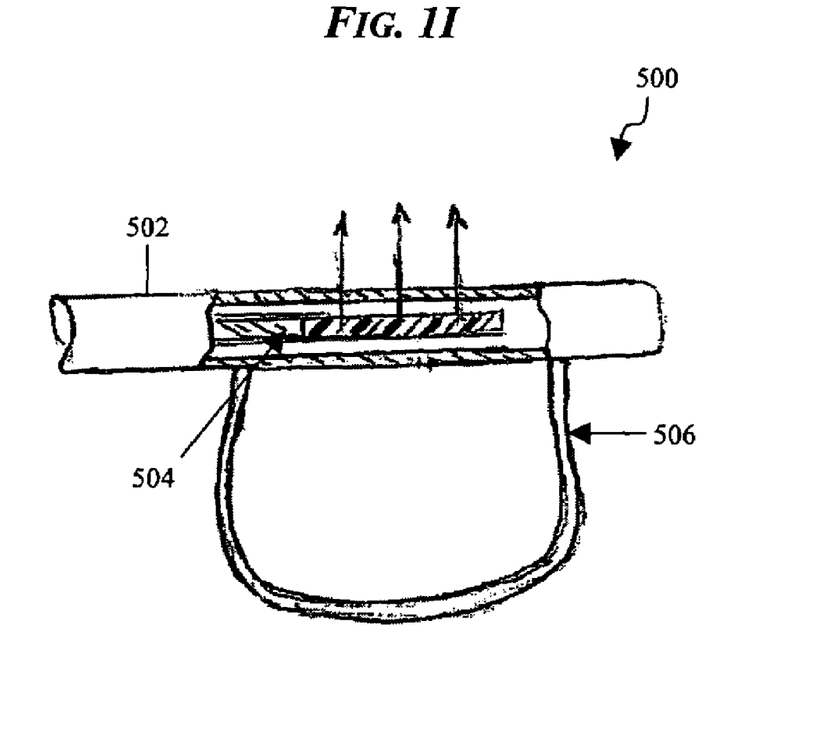
FIG. 1I is a schematic, partially cross-sectional view of another embodiment of a tip portion of an ablation instrument with an asymmetrical balloon disposed thereon in accordance with the present invention.

Four other exemplary ablation systems are shown in FIGS. 1F-1I. In the first embodiment shown in FIG. 1F, the instrument 200 is similar to instrument 10 in that it includes an outer housing 202 having an optical fiber 208 disposed therein. Ablation instrument 200, however, does not include a light scattering medium disposed therein. Rather, a reflector 204 is disposed within a distal end of the housing 202 and it is positioned at an angle that is effective to direct light from the fiber 208 in a sideways direction toward a target ablation site. The angle of reflection can, of course, vary depending on the intended use. FIG. 1G illustrates another embodiment of an ablation system 300. In this embodiment, the ablation system 300 is adapted to deliver ultrasound energy to form an ablative lesion. As shown, the system 300 includes an outer housing 302 having a curved transducer 304 disposed therein for focusing ultrasound into an ablative beam. The housing 302 can be configured to absorb or reflect energy, except for a portion of the housing 302 which forms a window 306 for allowing the ultrasound energy to pass therethrough. In yet another embodiment, shown in FIG. 1H, the ablation instrument 400 can be adapted to deliver radiofrequency (RF) or microwave energy. As shown, an RF or microwave transmitter 404 is disposed within a housing 402, and the housing 402 is configured to absorb or reflect RF or microwave energy, except for a window 406 formed therein for allowing the energy to pass therethrough. The energy is thus allowed to pass through the radiation transparent window 406 to form an ablative lesion. Referring to FIG. 1I, yet another embodiment of an ablation system 500 is shown. In this embodiment, the ablation system 500 includes a housing 502 having an asymmetrical balloon 506 formed on a distal end thereof. The balloon 506 can be filled with a radiation absorbing fluid to protect tissue disposed therearound, such as the coronary sinus, from ablative energy being transmitted from the energy-emitting element 504.

Figure 2:
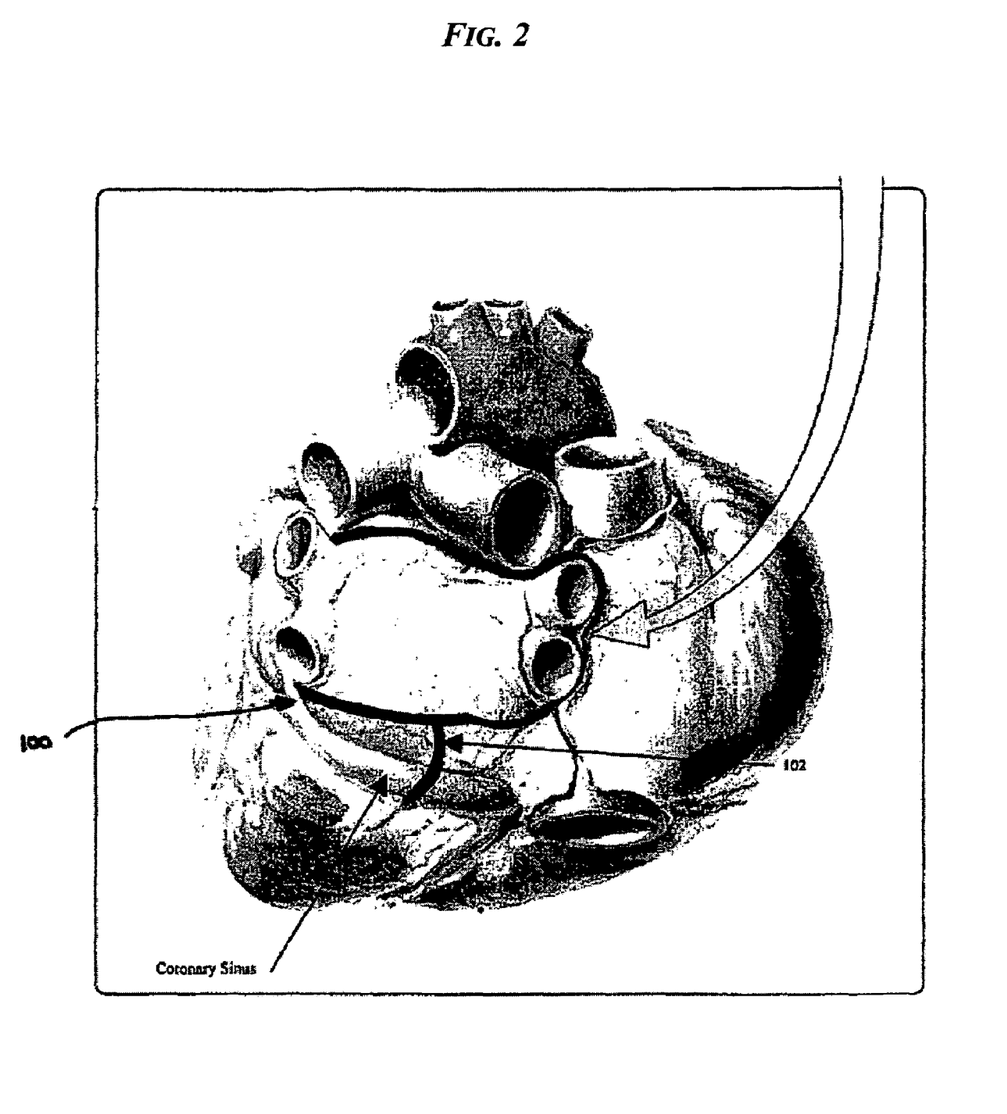
FIG. 2 illustrates a human heart showing the pulmonary veins in the left atrium and the coronary sinus.

The present invention also provides a method for ablating a lesion. While the method is described in connection with ablation instrument 10, a person skilled in the art will appreciate that virtually any ablation instrument can be used. In general, the method includes the steps of positioning an ablation instrument 10 within the coronary sinus and activating the instrument to form a lesion adjacent to the mitral valve annulus. In an exemplary embodiment, the lesion is formed in connection with a pulmonary vein encircling lesion, which is preferably formed using a separate ablation instrument, an exemplary embodiment of which is disclosed in U.S. Pat. No. 6,558,375 of Sinofsky et al. FIG. 2 illustrates a typical lesion set, which includes a first lesion 100 encircling the pulmonary veins, and a connecting lesion 102 extending to the mitral valve annulus, which is sometimes referred to as the "left isthmus block." In accordance with an exemplary embodiment of the present invention, the ablation instrument 10 can be positioned within the coronary sinus to form the lesion extending to the mitral valve annulus. This lesion is preferably formed while shielding the major portion of the sinus, itself, from ablative energy.

Figure 3:
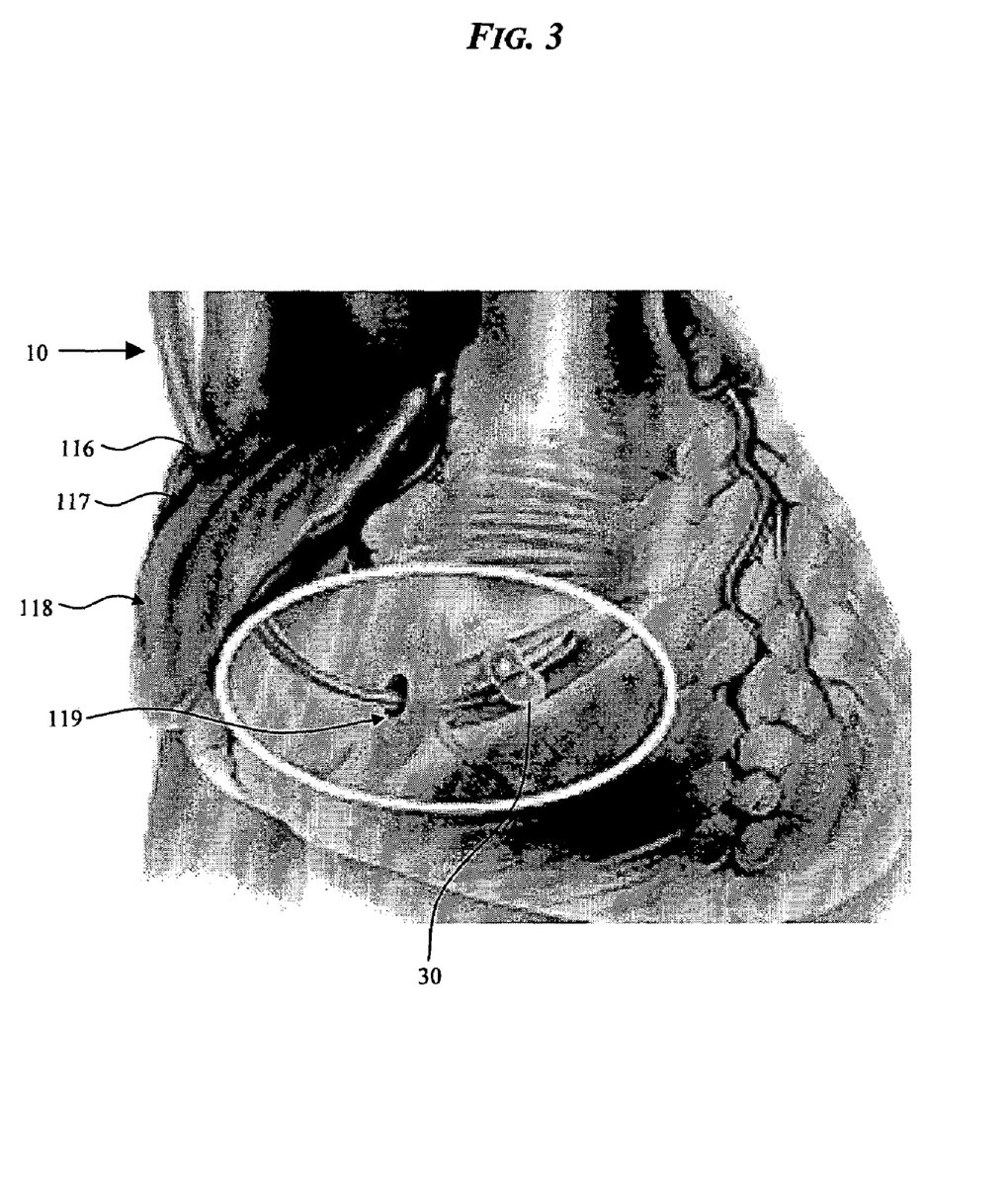
FIG. 3 illustrates an ablation instrument positioned within the coronary sinus of a heart in accordance with yet another embodiment of the present invention.

FIG. 3 illustrates one exemplary method for forming an ablative lesion in left atrial tissue adjacent the mitral valve annulus. The procedure is preferably performed on a beating heart, which can be accessed either using minimally invasive techniques, wherein a small incision is formed in the chest, or using conventional surgical techniques, wherein a sternotomy is performed. Once the heart is located, an incision 116 is formed in the right atrium 117, as shown. The ablation instrument 10 is then introduced through the incision 116 and it is guided through the right atrium 118 and into the coronary sinus 119. The outer housing 12 is preferably delivered first and it can be anchored within the coronary sinus 119 using, for example, balloon 30 to maintain the instrument 10 in a fixed position. A purse string suture (not shown) or other techniques known in the art can be used to secure the tissue around the incision 116 relative to the ablation instrument 10. Once the outer housing 12 is positioned within the coronary sinus 119, the ablative element 16 can be guided through the lumen 14 in the outer housing 12 to position the light-directing tip 20 adjacent to the target ablation site. As previously noted, an expandable element, such as balloon 30, can optionally be used to position the tip 20 at a desired location relative to the target ablation site. A person skilled in the art will appreciate that the light-directing tip 20 does not need to be slidably disposed within the housing 12, but that it can be fixedly disposed within the housing 12 or otherwise configured to be placed adjacent to the target ablation site.

Figure 4:
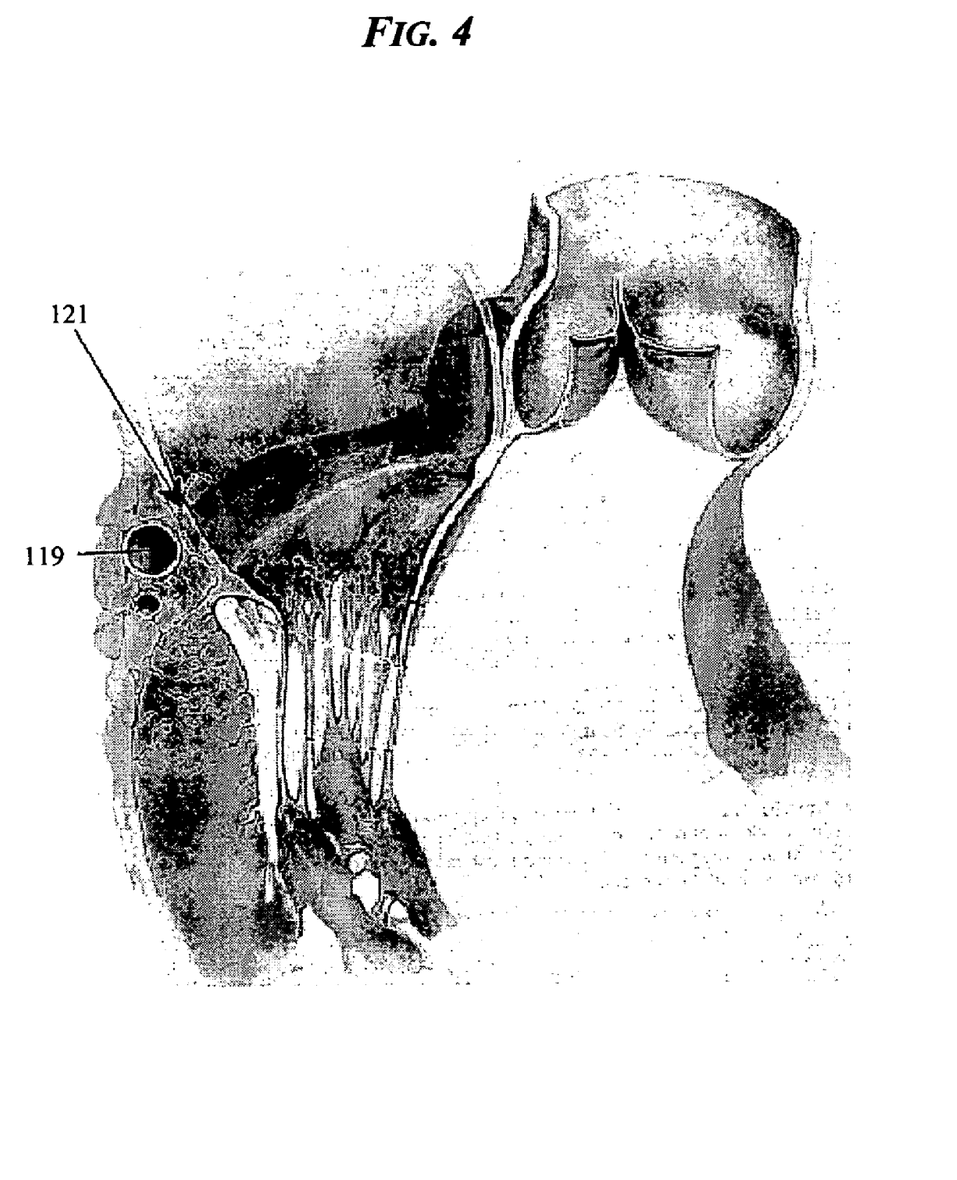
FIG. 4 illustrates the general location of a lesion to be formed using an instrument positioned within the coronary sinus in accordance with one embodiment of the present invention.

Once the ablation instrument 10 is properly positioned within the coronary sinus, the ablation instrument 10 can be activated to deliver ablative energy that is effective to form a lesion in left atrial tissue near the mitral valve annulus 121, as indicated in FIG. 4. The ablative energy is preferentially directed from within the coronary sinus 119 towards the heart rather than other portions of the coronary sinus that are not proximate to the heart. As noted above, the shape and size of the lesion will depend on the particular configuration of the ablation instrument, and a variety of ablation instruments can be used to form a lesion having a desired shape and size. The ablative energy source used to form the lesion can also vary. Suitable energy sources include, for example, RF heating, cryogenic cooling, ultrasound, microwave, ablative fluid injection and the like. RF Heating devices, for example, are described in U.S. Pat. No. 5,690,611 issued to Swartz et al. and herein incorporated by reference. Cryogenic devices are similarly described, for example, in U.S. Pat. No. 6,161,543 issued to Cox et al. and herein incorporated by reference.

When the penetrating energy is light, the source is activated to transmit light through the optical fiber 18 to the light-directing tip 20, wherein the light is scattered in a uniform diffuse pattern along the length of the tip 20. The reflective coating 24 and/or the reflective end 26 interact with the light scattering medium 22 to provide a substantially uniform distribution of light throughout the tip 20. In particular, when a mirrored end cap 26 is employed, as illustrated in FIG. 1A, light propagating through the light-directing tip 20 will be at least partially scattered before it reaches the mirror 26. When the light reaches the mirror 26, it is then reflected by the mirror 26 and returned through the tip 20. During the second pass, the remaining radiation encounters the scattering medium 22 which provides further diffusion of the light. Likewise, when a reflective coating or longitudinally disposed reflector 24 is used, as illustrated in FIGS. 1A and 1B, the light emitted by the diffusing tip 20 will be reflected toward the target ablation site to ensure that a uniform lesion is created. The reflective coating 24 is particularly effective in directing the light toward the target ablation site, thereby preventing the light from passing through the housing 12 around the entire circumference of the housing 12. The reflective coating 24 can also be effective to shield the coronary sinus from light, thereby preventing ablation of the coronary sinus.

In other embodiments, depending on the configuration of the light-directing tip 20, the ablative element 16 can optionally be moved during delivery of ablative energy to form a lesion having a desired shape. For example, wherein the light-directing tip 20 is configured to deliver a small spot-shaped beam of ablative energy, the ablative element 16 can be rotated about its elongate axis such that the spot-shaped beam can form a linear lesion in the heart wall.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for treating atrial fibrillation on a beating heart, the method comprising:
   positioning a portion of an ablation instrument within the coronary sinus;
   activating the ablation instrument to form an ablative lesion in left atrial tissue, the lesion extending to the mitral valve annulus; and
   forming a lesion encircling the pulmonary veins with a separate epicardial device;
   wherein the step of activating the ablation instrument further comprises directing ablative energy to form a lesion that extends from the lesion encircling the pulmonary veins to the mitral valve annulus.

2. A method for treating atrial fibrillation on a beating heart, the method comprising:
   positioning a portion of an ablation instrument within the coronary sinus;
   activating the ablation instrument to form an ablative lesion in left atrial tissue solely from within the coronary sinus, the lesion extending to the mitral valve annulus; and
   deploying an expandable balloon to secure the position of the ablation instrument within the coronary sinus during at least a portion of the ablation, wherein the balloon is asymmetrical to deliver ablative energy in a controlled direction.

3. A method for treating atrial fibrillation, the method comprising:
   forming an incision in the right atrial appendage of the right atrium;
   introducing a distal end of an ablation instrument though the incision and into the coronary sinus; and
   activating the ablation instrument to deliver ablative energy solely from within the coronary sinus to form a lesion extending from the pulmonary veins to the mitral valve annulus.

4. A method for treating atrial fibrillation, the method comprising:
   forming an incision in the right atrium;
   introducing a distal end of an ablation instrument though the incision and into the coronary sinus;
   activating the ablation instrument to deliver ablative energy to form a lesion extending from the pulmonary veins to the mitral valve annulus; and
   forming a lesion encircling the pulmonary veins with a separate epicardial device;
   wherein the lesion extending from the pulmonary veins to the mitral valve annulus extends to the lesion encircling the pulmonary veins.

* * * * *